United States Patent [19]
Gundling

[11] Patent Number: 5,817,798
[45] Date of Patent: Oct. 6, 1998

[54] RAPID RNA ISOLATION PROCEDURE IN THE PRESENCE OF A TRANSITION METAL ION

[75] Inventor: Gerard J. Gundling, Lake Forest, Ill.

[73] Assignee: Abbott Laboratories, Abbott Park, Ill.

[21] Appl. No.: 931,981

[22] Filed: Sep. 17, 1997

[51] Int. Cl.$^6$ .............................. C12P 19/34; C07H 21/02
[52] U.S. Cl. .................... 536/25.42; 435/91.3; 536/25.4; 935/20
[58] Field of Search .......................... 435/91.3; 536/25.4, 536/25.42; 935/20

[56] References Cited

U.S. PATENT DOCUMENTS

| | | |
|---|---|---|
| 4,483,920 | 11/1984 | Gillespie et al. . |
| 4,843,155 | 6/1989 | Chomczynski . |
| 4,847,165 | 7/1989 | Wreschner . |
| 5,063,162 | 11/1991 | Kiefer . |
| 5,234,809 | 8/1993 | Boom et al. . |

FOREIGN PATENT DOCUMENTS 0512767  11/1992  European Pat. Off. .

OTHER PUBLICATIONS

"QuickPrep® Total RNA Extraction Kit", Pharmacia Biotech (1996).

Aviv, H., et al., "Purification of Biologicallly Active Globin Messenger RNA by Chromatography on Oligothymidylic acid–Cellulose", *Proc. Nat. Acad. Sci. USA*, 69(6):1408–1412 (1972).

Castellino, F.J., et al., "The Denaturing Effectiveness of Guanidinum, Carbamoylguanidinium, and Guanylguanidinium Salts", *Biochemistry*, 7(11):4135–4138 (1968).

Chirgwin, J.M., et al., "Isolation of Biologically Active Ribonucleic Acid from Sources Enriched in Ribonuclease", *Biochemistry*, 18(24):5294–5299 (1979).

Chomczynski, P., "A Reagent for the Single–Step Simultaneous Isolation of RNA, DNA and Proteins from Cell and Tissue Samples", *BioTechniques*, 15(3):532–536 (1993).

Chomcyznski, P., et al., "Substitution of Chloroform by Bromochloropropane in the Single–Step Method of RNA Isolation", *Analytical Biochemistry*, 225:163–164 (1995).

Chomczynski, P., et al., "Single–Step Method of RNA Isolation by Acid Guanidinium Thiocyanate–Phenol–Chloroform Extraction", *Analytical Biochemistry*, 162:156–159 (1987).

Gillespie, D.H., et al., "Dissolve and capture: a strategy for analysing mRNA in blood", *Nature*, 367:390–391 (1994).

Hornes, E., et al., "Magnetic DNA Hybridization Properties of Oligonucleotide Probes Attached to Superparamagnetic Beads and Their Use in the Isolation of Poly(A) mRNA From Eukaryotic Cells", *GATA*, 7(6):145–150 (1990).

Kolbe, T., et al., "Detection of *bcrabl*Fusion mRNA is Samples of Whole, Unfractionated Blood", *Leukemia Research*, 18(6):465–468 (1994).

Porath, J., et al., "Metal chelate affinity chromatography, a new approach to protein fractionation", *Nature*, 258:598–599 (1975).

Thompson, J., et al., "Molecular Hybridization with RNA Probes in Concentrated Solutions of Guanindine Thiocyanate", *Analytical Biochemstry*, 163:281–291 (1987).

Primary Examiner—Gary L. Kunz
Attorney, Agent, or Firm—Paul D. Yasger

[57] ABSTRACT

Provided herein is a rapid method for isolating total RNA from test samples and further for isolating mRNA from test samples.

9 Claims, No Drawings

5,817,798

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 200 base pairs
        ( B ) TYPE: nucleic acid -continued (C) STRANDEDNESS: double
(D) TOPOLOGY: linear (ii) MOLECULE TYPE: genomic DNA (PSA exons 2 and 3)

(xi) SEQUENCE DESCRIPTION: SEQ ID NO:1:

| CGTGGATTGG | TGCTGCACCC | CTCATCCTGT | CTCGGATTGT | GGGAGGCTGG | 50 |
| GAGTGCGAGA | AGCATTCCCA | ACCCTGGCAG | GTGCTTGTGG | CCTCTCGTGG | 100 |
| CAGGGCAGTC | TGCGGCGGTG | TTCTGGTGCA | CCCCAGTGG | GTCCTCACAG | 150 |
| CTGCCCACTG | CATCAGGAAC | AAAAGCGTGA | TCTTGCTGGG | TCGGCACAGC | 200 |

(2) INFORMATION FOR SEQ ID NO:2:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:2:

GCACCCCTCA TCCTGTCTCG GATTGT                                26

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:3:

CCGACCCAGC AAGATCACGC TTTTGTT                               27

(2) INFORMATION FOR SEQ ID NO:4:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:4:

CAGGTGCTTG TGGC                                             14

RAPID RNA ISOLATION PROCEDURE IN THE PRESENCE OF A TRANSITION METAL ION

FIELD OF THE INVENTION

The present invention relates to nucleic acid purification and in particular, relates to purification of ribonucleic acid (RNA) and messenger RNA (mRNA).

BACKGROUND OF THE INVENTION

Interest in procedures for isolating or otherwise purifying nucleic acids from test samples, such as blood or serum, has increased since the introduction of nucleic acid amplification reactions such as PCR or LCR. Adaptations have been made to these amplification reactions such that they can be employed to detect a variety of diseases. While adaptations have been made to amplification procedures which allow for relatively rapid detection of diseases, preparation of the nucleic acids which are amplified by such procedures continues to be a limiting factor in terms of the overall time it takes to detect a disease using an amplification reaction based assay.

While many nucleic acid purification procedures are well known and have been in existence for years, these procedures can be time consuming and may employ reagents that present dangers to those performing the purification. For example, it has long been known that DNA and RNA readily can be obtained in a purified form from a test sample using organic extraction procedures, but such procedures can require several extractions and therefore can be time consuming. Additionally, the use of organic solvents is undesirable and dangerous if proper precautions are not followed.

More recently, nucleic acid purification procedures have exploited the affinity nucleic acids have for solid support materials, such as glass, in the presence of a chaotropic reagent. According to such procedures, a test sample comprising cellular or viral material can be contacted with a chaotropic reagent and a solid support material. The chaotropic reagent lyses any cells in the test sample to liberate the nucleic acid contained in the cells which is then captured on the solid support material. According to these procedures however, additional steps and reagents may be required to differentially purify DNA from RNA.

One procedure for selectively purifying messenger RNA (mRNA) from other nucleic acids takes advantage of the poly A tail typically found on strands of mRNA. In particular, a support material coated with a poly thymine oligonucleotide is employed to bind any mRNA in the original sample and therefore separate it from other species of nucleic acid such as DNA. "Oligo dT columns" are commonly used for this purpose. Although columns of this sort are effective, the amount of material passed over the column is relatively limited because the starting material is generally quite viscous due to the presence of DNA and RNA in addition to the desired mRNA in the starting material. mRNA can be purified from higher volumes of starting material, but methods for higher volume purifications usually resort to the use of preliminary organic extraction procedures to isolate the total RNA from DNA prior to separating mRNA from the total RNA with the oligo dT column. In addition to the problems presented by the use of organic solvents, procedures for differentially separating RNA from DNA leave the RNA in an insoluble state. As a result, once the total RNA is purified from the DNA it must be resolubilized prior to purifying the mRNA from the total RNA. Hence, in addition to the limitations presented by the use of organic solvents, these procedures require additional steps in order to enable further purification.

Accordingly, there is a need for a safe, effective and convenient method for separating total RNA from DNA as well as separating mRNA from other nucleic acid species that is not limited by the amount of starting material that can be purified.

SUMMARY OF THE INVENTION

The present invention provides methods for separating total RNA from other nucleic acid in a test sample and further provides methods for separating mRNA from total RNA. Advantageously, the method provided herein does not require use of organic solvents for separation of nucleic acid species and can be used on large scale samples. Hence, the method is safer and easier to perform than previously known methods.

According to one embodiment, the method is one for purifying or separating total RNA from other nucleic acid species that may be present in a test sample and comprises the steps of (a) contacting a test sample with a transitional metal ion having a valence of at least +2 to form a precipitant and a supernatant; (b) separating the precipitant from the supernatant; and (c) collecting the supernatant to thereby obtain a purified solution of total RNA. In cases where nucleic acids are contained within organisms such as virus particles or cells, the method may employ the additional step of exposing the test sample to a lytic agent prior to, at the same time, or after the test sample is contacted with a transitional metal ion.

According to another embodiment, mRNA can be separated from or purified from other nucleic acid species in a test sample. In accordance with this embodiment, total RNA is collected as above and mRNA is separated from the total RNA. Separating mRNA from the total RNA can be performed using methodologies well known in the art and oligo dT matrices are suitable for this purpose.

DETAILED DESCRIPTION OF THE INVENTION

As mentioned above, the present invention provides methods for separating total RNA from the total nucleic acid in a test sample, as well as separating mRNA from a test sample by separating mRNA from purified total RNA.

The term "total RNA" as used herein is intended to mean all RNA that may be present in a test sample. In other words, nucleic acid sequences made up of ribonucleotide monomers which may include, for example, genomic RNA, subgenomic RNA fragments, mRNA, transfer RNA (tRNA) and ribosomal RNA (rRNA). "Total nucleic acid", as used herein contemplates the total RNA contained in a test sample and nucleic acid sequences made up of deoxyribonucleotide monomers including, for example, genomic DNA, subgenomic DNA fragments and products from DNA amplification reactions.

A "test sample" is anything containing RNA or mRNA. The test sample is or can be derived from any biological source, such as for example, blood, serum, plasma, cerebral spinal fluid, milk, ascites fluid, synovial fluid, peritoneal fluid, amniotic fluid, tissue, fermentation broths, cell cultures and the like. The test sample can be used either (i) directly as obtained from the source or (ii) following a pre-treatment to modify the character of the test sample. Thus, the test sample can be pre-treated prior to use by, for example, preparing plasma from blood, disrupting cells or viral particles, amplifying nucleic acids, preparing liquids from solid materials, diluting viscous fluids, filtering liquids, distilling liquids, concentrating liquids, and the like.

The invention exploits the discovery that transitional metal ions having a valence of +2, or greater, effectively and selectively precipitates contaminants (e.g. substances other than total RNA) that may be present in a test sample. For example, in cases where the sample solution is derived from a biological source such as, for example blood, transitional metal ions having these properties effectively precipitate contaminants such as cellular debris and other proteins. Moreover, while such contaminants are precipitated, total RNA remains in solution and easily can be separated from the precipitated material. As a result the total RNA is recovered and mRNA can be purified from this solution directly by contacting it with, for example, an oligo dT matrix, without the use of organic solvents or the need to resolubilize the total RNA prior to contacting it with the oligo dT matrix.

Transitional metal ions having a valence of +2 or greater are those elements traditionally termed "transition elements" and have an oxidation state of +2 or more. While many of these elements have multiple valencies, the following ionic forms of the following elements are preferred: Cobalt ions ($Co^{+2}$ or $Co^{+3}$), Zinc ions ($Zn^{+2}$), Copper ions ($Cu^{+2}$), Vanadium ions ($V^{+2}$ or $V^{+3}$) and Nickel ions ($Ni^{+2}$). It will be understood, of course, that these ions can be contacted with a test sample through the use of a solution of salts of these elements which thereby contain these ions. For example, sulfate and chloride salts of these ions are readily available and can be solubilized to form solutions of the aforementioned ions. Typically, solutions containing concentrations of these ions greater than 5 mM are employed, preferably the concentration is between 10 mM and 500 mM, and more preferably the concetration of such ions is between 15 mM and 150 mM.

While test samples may contain only dissolved nucleic acids with few other contaminants, and therefore be relatively "clean", some test samples may contain intact cells or virus particles from which nucleic acids need to be released. A variety of methods and reagents for releasing nucleic acids from cells and virus particles are well known and a matter of choice for one skilled in the art. Such reagents or methods will be referred to herein as "lytic agents". For example, some chemical methods for lysing cells or virus particles include but are not limited to contacting cells or virus particles with a buffer containing a denaturant such as chaotropes, detergents or urea. Such denaturants are usually at a concentration of at least 1 M and typically at a concentration of between about 2M and about 5 M in a buffered solution having a neutral pH of between about 6 and about 8. Additionally, alkaline solutions having a pH of greater than about 8.5 are known to disrupt cell walls or viral coats of various organisms and can therefore also be employed as lytic agents. Similarly, acidic solutions having a pH of less than about 5 also can be employed as lytic agents because of their ability to disrupt cell walls or viral coats.

Buffers containing chemical lytic agents may also comprise other ingredients which may, for example, create a stable environment for nucleic acids released from cellular or viral materials. Such other ingredients may include salts such as lithium acetate or sodium chloride; or detergents such as N-lauroylsacrosine or TWEEN.

Alternatively, lytic agents may be in the form of mechanical means for lysing cells or virus particles to thereby release nucleic acids. Such means are readily available and may include homogenizers, sonicators or bead beaters. Hence, according to the present invention, a test sample can be treated to denature entities containing nucleic acids prior to, concomitantly with, or after contacting the sample with a transitional metal ion having a valence of +2 or more.

Upon releasing nucleic acids from an entity containing them, if necessary, and contacting the test sample with a transitional metal ion having a valence of +2 or greater to thereby precipitate DNA and, if necessary, other cellular material, the total RNA can be separated from the precipitate. As alluded to above, the total RNA remains in solution and is part of the supernatant and collecting the supernatant provides a solution of total RNA that can be further purified to collect mRNA from the total RNA. Separating and collecting the supernatant can be accomplished in a variety of ways known to those skilled in the art. For example, separation and collection of the supernatant can be achieved through centrifugation, filtration or simply allowing the precipitate to sediment and pipetting the supernatant away from the sedimented precipitate.

Once the supernatant is separated and collected, it can be further processed to recover mRNA from the total RNA. mRNA can be collected from total RNA using a specific binding member bound to a solid support material. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; as well as complementary nucleic acid sequences or analogs thereof. "Solid support materials" as used herein, refers to any material which is insoluble, or can be made insoluble by a subsequent reaction. The solid support material can be chosen for its intrinsic ability to attract and immobilize a polynucleotide, or alternatively, the solid phase can retain an additional receptor which has the ability to attract and immobilize a polynucleotide. The solid phase thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art. Solid support materials also can comprise porous materials such as, for example, natural polymeric carbohydrates and their synthetically modified, crosslinked or substituted derivatives, such as agar, agarose, or cross-linked alginic acid. All of these materials may be used in suitable shapes or forms such as, for example, films, sheets, plates, beads, microparticles and the like.

Hence, using a solid support bound specific binding member, mRNA can be isolated from total RNA directly such as when a sequence specific for a particular mRNA sequence is bound to the support material. Alternatively, a sequence specific for a particular mRNA sequence can be derivatized with another specific binding member such as, for example an antigen, that specifically binds an antibody on the solid support material. Solid support materials having immobilized oligonucleotides containing sequences typically in the range of between about 10–50 thymine residues are well suited for purposes of purifying mRNA from total RNA. In particular, such thymine polynucleotides serve as affinity reagents for adenine polynucleotide residues generally found on mRNA. One particular example of such a coated solid support includes an oligo dT column.

When desired, mRNA bound to a solid support material by virtue of a specific binding member, can be eluted from the support material using a variety of methods well known to those skilled in the art, such as by changing the temperature or ionic strength in the environment of the solid support material. As a further alternative, while mRNA can be eluted from an oligo dT column using a variety of techniques well known to those skilled in the art, mRNA simply can be eluted with water.

The following examples are provided to further illustrate the present invention and are not intended to limit the invention.

EXAMPLES

The following examples demonstrate mRNA isolation by the rapid and efficient method of the instant invention. This method was compared to two known methods in the art, one using RNAZol and a second using oligo dT coated microparticles, to isolate mRNA from cells in whole blood. The Lymph Node Carcinoma of the Prostate (LNCaP) cell line was chosen as the experimental sample, with RT/PCR utilized to detect the prostate specific antigen (PSA) mRNA product from all the methods. The RT/PCR method used DNA oligomer primers and probes specific for PSA mRNA from exons 2 and 3 of the PSA gene.

Example 1
LNCaP Cell Sample Preparation

Lymph Node Carcinoma of the Prostate (LNCaP) cells are human prostatic adenocarcinoma cells from a metastatic cell line. The LNCaP cell line was obtained from American Type Culture Collection, ATCC #1740-CRL, Rockville, Md. The LNCaP cell sample was prepared by first decanting the tissue culture media from the adherent LNCaP cells in tissue culture. Cells were rinsed with saline, then trypsinized for 3 minutes at 37° C. to remove them from the tissue culture flask. Additional tissue culture media (RPMI-1640 containing 10% fetal calf serum) was added to the flask and the cells were resuspended and poured into a centrifuge tube. Cells were centrifuged at 200×g for 5 minutes at room temperature. Pelleted cells were resuspended in cold RPMI-1640 containing 0.5% bovine serum albumin (BSA), then passed through a nylon filter which had been prewetted with cold RPMI-1640/BSA. Cells were counted on the Cell-Dyn automated hematology analyzer, and adjusted to $1 \times 10^5$ cells/ml in Phosphate Buffered Saline (PBS).

A unit of whole blood was placed on a rocker for 10 minutes to mix to ensure homogeneity, then divided into 4×100 ml aliquots. LNCaP cells were serially diluted in PBS then spiked into the aliquots of whole blood to give final concentrations of 1, 10 or 100 LNCaP cells/ml of whole blood. No LNCaP cells were added to one of the 100 ml aliquots of whole blood for use as a negative control. All 100 ml aliquots were then mixed and further divided into 5 ml aliquots.

Example 2
mRNA Isolation using the Method of the Invention

Cells were lysed from duplicates of the 5 ml aliquots containing 0, 1, 10 and 100 LNCaP cells/ml whole blood, prepared in Example 1, by mixing each aliquot with an equal volume of 2×Lysis Buffer consisting of 4.5M guanidine isothiocyanate, 1M lithium acetate and 2 % N-lauroylsarcosine, and vortexing. Ten ml (equal to the total previous volume) of Precipitation Solution consisting of 1 X Lysis Buffer (2.25M guanidine isothiocyanate, 0.5M lithium acetate, 1% N-lauroylsarcosine) containing 100 mM cobalt chloride ($CoCl_2$) to precipitate cellular contaminants, was then added, vortexed, and allowed to precipitate for 30 minutes. The mixture was centrifuged at 1000×g for 30 minutes to remove precipitant containing cell debris.

The supernatant containing the solubilized mRNA was applied to a 20 mg oligo-dT cellulose column (Collaborative Biomedical Product Type T3, #20003, Bedford, Mass.) on a Promega Vac-Man (Promega, Madison, Wis.) vacuum manifold. The column was washed with 5 ml of 1×Lysis Buffer, followed by 5 ml of 100 mM NaCl in 10 mM Tris, pH 7.2. The column was then transferred to a microfuge tube and centrifuged to remove residual fluid. The column was washed twice with 200 $\mu l$ of 100 mM NaCl in 10 mM Tris, pH 7.2. The column was transferred to a fresh microfuge tube and the mRNA was eluted with 3 volumes of 75 $\mu l$ each (total 225 $\mu l$) of Molecular Biology grade water. The entire procedure was carried out at room temperature.

Example 3
mRNA Isolation using RNAZol

Cells were isolated from duplicates of the 5 ml aliquots containing 0, 1, 10 and 100 LNCaP cells/ml whole blood, prepared in Example 1, using Ficoll-hypaque, then washed with 10 ml PBS. Cells were pelleted by centrifugation for 10 minutes at 2000 rpm in a Beckman J6 centrifuge and resuspended in 1 ml PBS. The resuspended cells were transferred to a microcentrifuge tube and pelleted by microfuging for 5 to 10 minutes.

The pellet was dissolved in RNAZol (Tel-Test, Inc., Friendswood, Tex.) following the manufacturer's directions, and the RNA was purified using the following method. One hundred $\mu l$ of molecular biology grade chloroform was added to 1 ml of the RNAZol mixture and vortexed for 50 seconds, then placed on ice for 5 minutes. After microfuging for 15 minutes the aqueous layer was removed and placed into a new microfuge tube. An equal volume of cold isopropanol was added and the mixture was vortexed for 15 seconds, then incubated overnight at $-20°$ C. to precipitate the RNA. Following precipitation the mixture was microfuged at 14,000×g for 30 minutes at 4° C. to pellet the precipitate. One ml of cold 75% ethanol was then added to the pellet and the mixture was vortexed until the pellet floated, then microfuged at 14,000×g for 15 minutes at 4° C. to pellet the precipitate. Another 1 ml of cold 75% ethanol was again added to the pellet, the mixture vortexed, then microfuged as before. After decanting and blotting any excess fluid from the tube, the pellet was allowed to air dry for 30 minutes, then dissolved in 12 $\mu l$ RNase free water. Purified RNA was quantitated by spectrophotometry using an absorbance reading at 260 nm and an extinction coefficient of 40. The sample was then diluted to contain 1 $\mu g$ of RNA in 25 $\mu l$ RNase free water.

Example 4
mRNA Isolation using oligo dT Microparticles

Cells were lysed from duplicates of the 5 ml aliquots containing 0, 1, 10 and 100 LNCaP cells/ml whole blood, prepared in Example 1, by mixing each aliquot with an equal volume of 2×Lysis Solution consisting of 4M guanidine isothiocyanate, 8 mM dithiothreitol, 1% sarcosyl, 1% Triton X-100, 100 mM NaCl in 20 mM MOPS, pH 7.0, until lysis occurred (approximately 30 seconds).

mRNA was then isolated by adding 120 $\mu l$ of Dynal oligo $(dT)_{25}$ magnetic microparticles (Dynal catalogue #610.05, Oslo, Norway), which had been prewashed and resuspended in 1×Lysis Solution (2M guanidine isothiocyanate, 4 mM dithiothreitol, 0.5% sarcosyl, 0.5% Triton X-100, 50 mM NaCl in 10 mM MOPS, pH 7.0), to each lysed sample and rocking for 15 minutes. Samples were centrifuged for 5 minutes at 2500 rpm in a Beckman GS-6R centrifuge.

Pelleted microparticles (beads) were washed by resuspending them in 0.5 ml 1×Lysis Solution. Using the Dynal magnetic rack (Dynal catalogue #190.02, Oslo, Norway), beads were captured and wash solution aspirated. Beads were washed with an additional 0.5 ml 1×Lysis Solution, captured and wash solution aspirated. Beads were then washed twice with 200 μl cold Wash Solution B (10 mM MOPS, pH 7.0 containing 50 mM NaCl, 0.5 % Triton X-100) by gently vortexing to resuspend, followed by capturing the beads using the magnetic rack, aspirating the wash solution and repeating. The beads with the mRNA bound were then resuspended in 25 μl of a cold solution of 16S and 23S rRNA (Boehringer Mannheim, catalogue #206938, Indianapolis, Ind.) diluted to 20 ng/ml in water.

Example 5
PSA mRNA Detection by RT/PCR

The amount of PSA mRNA present in each of the 4 aliquots prepared by the 3 different methods in Examples 2, 3 and 4 above, was determined by RT/PCR and oligonucleotide hybridization with labeled probe as described in U.S. patent application Ser. No. 08/514,704 filed Aug. 14, 1995 which is herein incorporated by reference. The target-specific primers and probe were designed to detect an mRNA target sequence (SEQ. ID. NO. 1) from exons 2 and 3 of the PSA gene by oligonucleotide hybridization PCR. The upstream primer (SEQ. ID. NO. 2) is found in exon 2 of the PSA gene, and the downstream primer (SEQ. ID. NO. 3) contains two nucleotides which hybridize at the 3' end of exon 2, with the remainder of primer nucleotides hybridizing with the contiguous mRNA region from exon 3 of the PSA gene. The detection probe (SEQ. ID. NO. 4) is found in exon 2 of the PSA gene and was designed as an internal hybridization probe for the amplified PSA target sequence.

Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference. The probe sequence also was synthesized using standard oligonucleotide synthesis methodology and haptenated with a carbazole at the 3' end and a carbazole at the 5' end using standard cyanoethyl phosphoramidite coupling chemistry as described in U.S. Pat. No. 5,464,746 incorporated herein by reference.

The RNA samples resulting from Examples 2, 3 and 4 above, were reverse transcribed, PCR amplified and detected using the PSA primers and PSA detection probe described above, as follows: Recombinant Thermus thermophilus polymerase was used at a concentration of 5 units/reaction, with dATP, dGTP, dTTP and dCTP present at a final concentration of 0.15 mM each, and dUTP present at a final concentration of 0.2 mM in a total reaction volume of 0.2 ml. All reactions were performed using 5×Bicine buffer, pH 8.24, consisting of 50 mM Bicine, 92 mM potassium acetate, 19 mM potassium hydroxide, 0.868M glycerol, at a final concentration of 1×. The reaction mixtures used primers at a concentration of 125 nM each, a probe concentration of 5 nM, and a final concentration of 2.5 mM manganese acetate. Testing was done on duplicate samples using 25 μl.

Reaction mixtures were first incubated at 68° C. for 60 minutes to reverse transcribe the RNA, followed by PCR amplification by incubation at 94° C. for 2 minutes, then cycling at 94° C. for 60 seconds/66° C. for 80 seconds for 40 cycles in a Perkin-Elmer 480 Thermal Cycler. After the reaction mixtures were thermal cycled, the mixtures were maintained at 97° C. for 5 minutes and probe oligo hybridization was accomplished by lowering the temperature to 15° C. in approximately two minutes. Following probe hybridization, samples were held at 15° C. for up to 24 hours before being tested.

Reaction products were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products, The results from this experiment (calculated as counts/second/second; c/s/s) are presented in TABLE 1 and show detection of PSA mRNA from LNCaP cells by the various methods employed.

TABLE 1

| LNCaP cells/ml | LCx ® rate (c/s/s) | | |
|---|---|---|---|
| whole blood | Example 2 | Example 3 | Example 4 |
| 0 | 35.3 | 28.5 | 43.2 |
| 0 | 32.2 | 27.5 | 65.5 |
| 1 | 720.9 | 378.0 | 62.6 |
| 1 | 550.4 | 403.1 | 55.9 |
| 10 | 1216.1 | 1231.0 | 1180.8 |
| 10 | 1249.0 | 1199.1 | 183.4 |
| 100 | 1290.1 | 1246.4 | 1287.6 |
| 100 | 1444.9 | 1363.9 | 1270.0 |

The method of the current invention proved to be the most sensitive of the 3 methods for detecting PSA mRNA as shown by its having the highest LCx® rate at the 1 LNCaP cell/ml concentration. This method also involved the least sample handling and was the quickest to perform; mRNA was isolated within approximately 90 minutes by this procedure, whereas the RNAZol procedure (Example 3) required 2 days, and the oligo-dT microparticle method (Example 4) took approximately 2 hours to complete.

While the invention has been described in detail and with reference to specific embodiments, it will be apparent to one skilled in the art that various changes and modifications may be made to such embodiments without departing from the spirit and scope of the invention.

What is claimed is:

1. A method for purifying RNA comprising the steps of:
    (a) contacting the test sample with a transitional metal ion having a valence of at least +2 to form a precipitant and a supernatant;
    (b) separating the precipitant from the supernatant; and
    (c) collecting the supernatant to thereby obtain a purified solution of total RNA.

2. The method of claim 1 further comprising the step of separating mRNA from said total RNA.

3. The method of claim 2 wherein said separating step comprises contacting said supernatant with an oligo dT matrix.

4. The method of claim 2 wherein said separating step comprises contacting said supernatant with a specific binding member bound to a solid phase.

5. The method of claim 4 wherein said specific binding member is a nucleic acid sequence, or an analog thereof, specific for a particular mRNA sequence.

6. The method of claim 1 wherein said bivalent metal ion is selected from the group consisting of $Co^{+3}$, $Co^{+2}$, $Zn^{+2}$, $Cu^{+2}$, $V^{+2}$ and $Ni^{+2}$.

7. The method of claim 1 wherein said bivalent metal ion is at a concentration of greater than 5 mM.

8. The method of claim 1 wherein prior to or concomitantly with step (a), said test sample is contacted with a lytic agent.

9. The method of claim 8 wherein said lysing agent comprises a chaotropic agent, a salt and a detergent.

* * * * *